United States Patent [19]
Yang

[11] Patent Number: 6,069,964
[45] Date of Patent: May 30, 2000

[54] EARPHONE-MICROPHONE-EARMUFF ASSEMBLY

[75] Inventor: Bill Yang, Taipei, Taiwan

[73] Assignee: Cotron Corporation, Taipei, Taiwan

[21] Appl. No.: 09/115,056

[22] Filed: Jul. 14, 1998

[30] Foreign Application Priority Data

Jun. 15, 1998 [TW] Taiwan ................................ 87209477

[51] Int. Cl.⁷ ................................................ H04R 26/00
[52] U.S. Cl. .............................. 381/374; 2/209; 379/430; 381/371
[58] Field of Search ........................ 2/209, 900; 379/430; 381/370–374, 376, 379, 381–383, FOR 149, FOR 150

[56] References Cited

U.S. PATENT DOCUMENTS

| | | | |
|---|---|---|---|
| 4,472,607 | 9/1984 | Houng | 381/379 |
| 4,542,803 | 9/1985 | Houng | 381/379 |
| 4,546,215 | 10/1985 | Ferraro | 381/374 |
| 4,669,129 | 6/1987 | Chance | 381/372 |
| 5,033,094 | 7/1991 | Hung | 381/379 |
| 5,285,530 | 2/1994 | Nardone, Jr. | 2/209 |
| 5,860,166 | 1/1999 | Ritts | 2/209 |
| 5,983,399 | 11/1999 | Falco et al. | 2/209 |

*Primary Examiner*—Curtis A. Kuntz
*Assistant Examiner*—Dionne N. Harvey
*Attorney, Agent, or Firm*—Thomas, Kayden, Horstemeyer & Risley

[57] ABSTRACT

The main components of an earphone-microphone-earmuff assembly are an earphone, a microphone and an earmuff. Besides using the assembly as a whole, each component can be independently used as well. The assembly has several pairs including a mounting cap, an earphone, an earmuff, and each part has its own mounting structure or structures for interconnection. In operation, the mounting cap and the earphone can be assembled together just for listening. Alternatively, the mounting cap and the earmuff can be assembled together just for ear warming or noise shielding. However, the mounting cap, the earmuff and the earphone can all be put together for hearing, ear warming and noise shielding. Furthermore, a microphone can also be installed on the earphone for easy communication.

20 Claims, 5 Drawing Sheets

EARPHONE-MICROPHONE-EARMUFF ASSEMBLY

CROSS-REFERENCE TO RELATED APPLICATION

This application claims the priority benefit of Taiwan application Ser. No. 87209477, filed Jun. 15, 1998, the full disclosure of which is incorporated herein by reference.

BACKGROUND OF THE INVENTION

1. Field of Invention

The present invention relates to a type of earphone-microphone-earmuff assembly. More particularly, the present invention relates to a type of earphone-microphone-earmuff assembly whose components can be used together, in various combinations or individually.

2. Description of Related Art

Following the recent progress in consumer electronics, electrical products are becoming more lightweight and miniaturized. Nowadays, people can carry various kinds of mini-electronic products such as Walkmans and recorders around and listen to music through earphones wherever they go without interfering with other people. Recently, even mobile telephone technology has developed hands-free communication by employing earphones and a microphone.

On the other hand, harsh winter seasons in some places cause temperatures to drop below freezing. Besides wearing very thick clothes, earmuffs are sometimes worn over the ears as a means of protection. At present, earmuffs and earphones are separately designed and no consideration has been made regarding their use together. Therefore, when both the earmuffs and earphones have to be used in wintertime, the simultaneous use is clumsy and inconvenient.

In light of the foregoing, there is a need to provide an earphone-microphone-earmuff assembly.

SUMMARY OF THE INVENTION

Accordingly, the present invention is to provide an earphone-microphone-earmuff assembly whose earphone and earmuff can be separated from each other or assembled together. Consequently, user can use the earphone or the earmuff individually or else use the earphone and the earmuff together as a unit. Furthermore, a microphone can be added to the assembly, too.

To achieve these and other advantages and in accordance with the purpose of the invention, as embodied and broadly described herein, the invention provides an earphone-microphone-earmuff assembly. The assembly mainly comprises of a mounting cap, an earphone and an earmuff. In addition, a microphone can be mounted next to the earphone.

The mounting cap has an external mounting structure and an internal mounting structure. The external mounting structure of the mounting cap is used to form a mechanical connection with an earphone clamping bar. The earphone also has an external mounting structure, and the earmuff has an external mounting structure and an internal mounting structure as well.

The mounting cap, the earphone and the earmuff can be assembled together in the following ways:

1. The internal mounting structure of the mounting cap and the mounting structure of the earphone are engaged when only the earphone is required.
2. The internal mounting structure of the mounting cap and the external mounting structure of the earmuff are engaged when only the earmuff is required.
3. The internal mounting structure of the mounting cap and the external mounting structure of the earmuff are engaged. In addition, the internal mounting structure of the earmuff and the mounting structure of the earphone are also engaged. Hence, the earphone and the earmuff can be used at the same time.

According to one embodiment of this invention, the external mounting structure of the mounting cap is a ball joint and the terminal of the earphone clamping bar is a ball socket. After the ball joint and the ball socket are joined together, the earphone-microphone-earmuff assemblies can be adjusted to make any desired angle with the earphone clamping bar, to fit the facial curvature and ear shape of each individual. Moreover, the earphone clamping bar extends between the earphones, from the back of the ears and around the back of the head, in the vicinity of the occipital ridge of the skull.

The internal mounting structure of the mounting cap and the earmuff can be a female Velcro tape, whereas the external mounting structure of the earmuff and the mounting structure of the earphone can be a male Velcro tape.

The earphone further includes a speaker and a speaker box. The speaker is installed within the speaker box and is connected to an audio source through a plug and a wiring cable. The mounting structure of the earphone is fixed to the exterior surface of the speaker box. Furthermore, a portion of the speaker box that touches the ear is wrapped using cushioning material for extra comfort.

The earmuff further includes an inner flap and an earmuff warmer. The inner flap is completely enclosed within the earmuff warmer.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Figure 1:
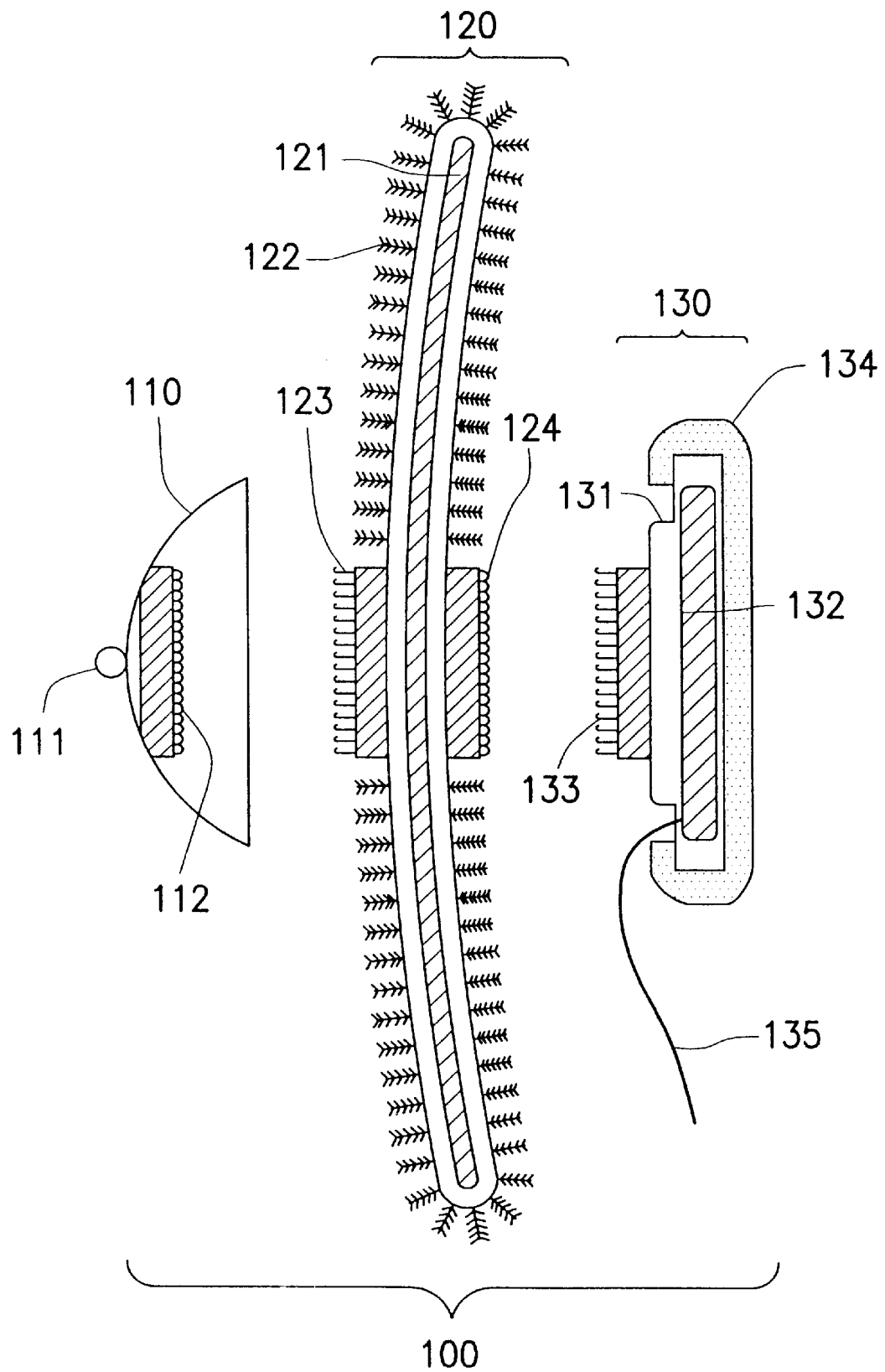
FIG. 1 is a sketch showing the components of an earphone-microphone-earmuff assembly according to one preferred embodiment of this invention.

Reference will now be made in detail to the present preferred embodiments of the invention, examples of which are illustrated in the accompanying drawings. Wherever possible, the same reference numbers are used in the drawings and the description to refer to the same or like parts.

FIG. 1 is a sketch showing the components of an earphone-microphone-earmuff assembly according to one preferred embodiment of this invention. The main components of an earphone-microphone-earmuff assembly 100 include a mounting cap 110, an earphone 130 and an earmuff 120.

Figure 2:
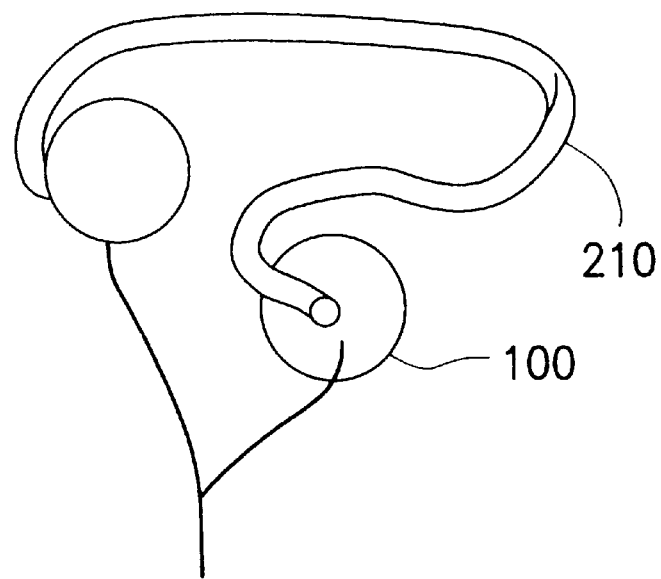
FIG. 2 is a sketch showing the earphone clamping bar of an earphone-microphone-earmuff assembly according to this invention.

The mounting cap 110 has an arc-shaped external casing. The mounting cap 110 is a special component, serving as a connection to other components of the earphone-microphone-earmuff assembly 100 as well as serving as a component for connecting to an earphone clamping bar so that the whole unit can be worn by a user. An earphone clamping bar 210 is shown in FIG. 2. The mounting cap 110 has two mounting structures. One mounting structure 111 of the mounting cap 110 is located outside the cap while the other mounting structure 112 is located inside the cap. The external mounting structure 111 of the mounting cap 110 is capable of connecting with the pivot joint at one end of the earphone clamping bar 210.

Therefore, the mounting cap 110 has three rotational degrees of freedom. For example, the external mounting structure 111 can be a ball joint while the pivot joint at the end of an earphone clamping bar can be a ball socket (not shown in the figure). After the ball and socket are joined together, the entire earphone-microphone-earmuff assembly 100 can move in an up-down or left-right direction to fit the particular head shape and facial features of individual user.

Figure 3:
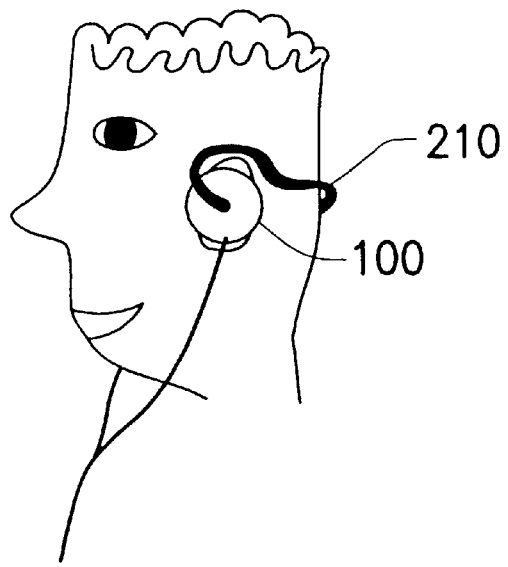
FIG. 3 is a sketch showing an earphone-microphone-earmuff assembly mounted onto an earphone clamping bar and the whole assembled unit worn by a user.

The earphone clamping bar 210 has a design that is different from conventional head-mounted earphones. Since every user has a different head shape, the head-to-ear length of each person may be different. Hence, the earphone clamping bar of a conventional head-mounted earphone must have adjusting mechanism allowing extension or retraction of its length. FIG. 3 is a sketch showing an earphone-microphone-earmuff assembly 100 mounted onto an earphone clamping bar 210.

As shown in FIG. 3, the assembled unit is mounted onto a user's head so that the earphone clamping bar 210 runs around the back of head, in the vicinity of the occipital ridge of the skull. This design arrangement avoids disturbing a user's hair when the assembly is worn. In addition, the shape and curvature of the earphone clamping bar 210 is ergonomically designed to fit the shape around the back of the ear for extra comfort. Moreover, since the curvature of the back of heads does not vary too much from person to person, a single length earphone clamping bar 210 can be used to fit most individuals. Consequently, a length-adjusting mechanism for the earphone clamping bar 210 is unnecessary.

The internal mounting structure of a mounting cap 110 can be engaged to an earphone 130 or an earmuff 120. The earphone 130 and the earmuff 120 have mounting structures for mutual engagement or for engagement with the mounting cap 110. These mounting structures can be some kind of snap-in mechanism or a piece of Velcro magic tape. In general, Velcro magic tape can be divided into two main types, namely a male tape and a female tape. The male tape and the female tape stick together.

Since the internal mounting structure 124 of the earmuff 120 may contact the ear, user's comfort will dictate the use of male/female type of Velcro tapes in different locations. For example, for better comfort, the internal mounting structure 112 of the mounting cap 110 and the internal mounting structure 124 of the earmuff 120 use female Velcro tapes. On the other hand, the mounting structure 133 of the earphone and the external mounting structure 123 of the earmuff use male Velcro tapes.

The earmuff 120 mainly includes a flexible arc-shaped inner flap 121 and an earmuff warmer 122 completely enclosing the inner flap 121. The inner flap provides some degree of stiffness and flexibility to the earmuff warmer 122. Hence, the earmuff warmer 122 is capable of covering user's ear snugly, keeping out cold air and shielding against noise. Outside the earmuff warmer 122, there are mounting structures 123 and 124. The mounting structure 123 is used for engaging the mounting cap 110, whereas the mounting structure 124 is used for engaging the earphone 130.

The earphone 130 mainly includes a speaker 132 installed inside a speaker box 131. On the backside of the speaker box 131, there is a mounting structure 133 capable of engaging with the mounting structure of the mounting cap 110 or the earmuff 120. These mounting structures can be the aforementioned Velcro magic tapes. Because one side of the speaker box 131 comes into contact with the user's ear, that side of the speaker box 131 is wrapped to form an ear cushion 134 for increased comfort. In general, the ear cushion 134 is made of sponge.

Figure 4:
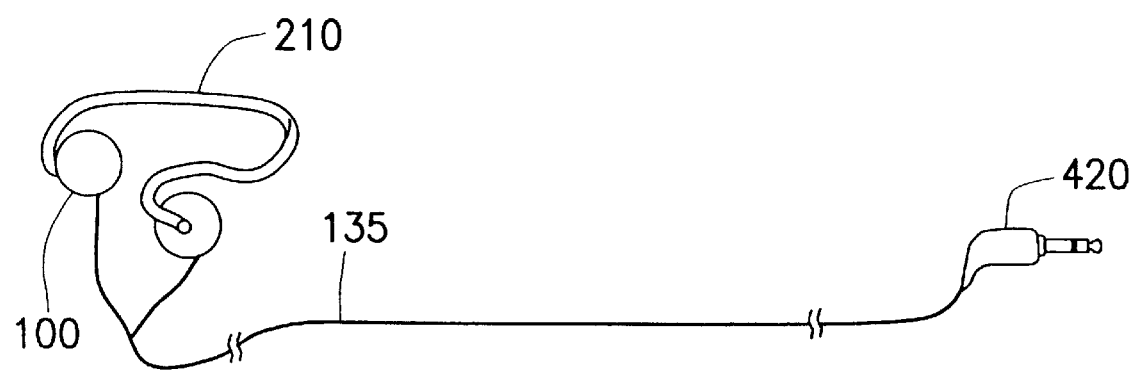
FIG. 4 is a sketch showing the plug and wiring cable running out of an earphone-microphone-earmuff assembly according to this invention.

FIG. 4 is a sketch showing the plug and wiring cable running out of an earphone-microphone-earmuff assembly according to this invention. As shown in FIG. 4, the speaker 132 has a wiring cable 135 and a plug 420. The plug 420 can be connected to any audio source such as hi-fi equipment, amplifiers or a mobile telephone. Since different equipment requires different plugs, shape of the plug can be selected accordingly.

Depending on user's need, the three main components of an earphone-microphone-earmuff assembly 100 can be combined in different ways as follows:

1. When user only wishes to hear a radio broadcast or music through the earphone, the mounting cap 110 and the earphone 130 are assembled together.
2. When the user only wishes to keep cold, damp air and noise out of the ear, the mounting cap 110 and the earmuff 120 are assembled together. In addition, when the earmuff 120 is used, the user can still place the usual in-ear type of earphone into the ear.
3. When the user wishes to simultaneously hear music, as well as keep cold damp air and noise out of his or her ears, the mounting cap 110 and the earmuff 120 are assembled first. This is followed by engaging the internal mounting structure 124 of the earmuff 120 with the mounting structure 133 of the earphone 130.

Figure 5:
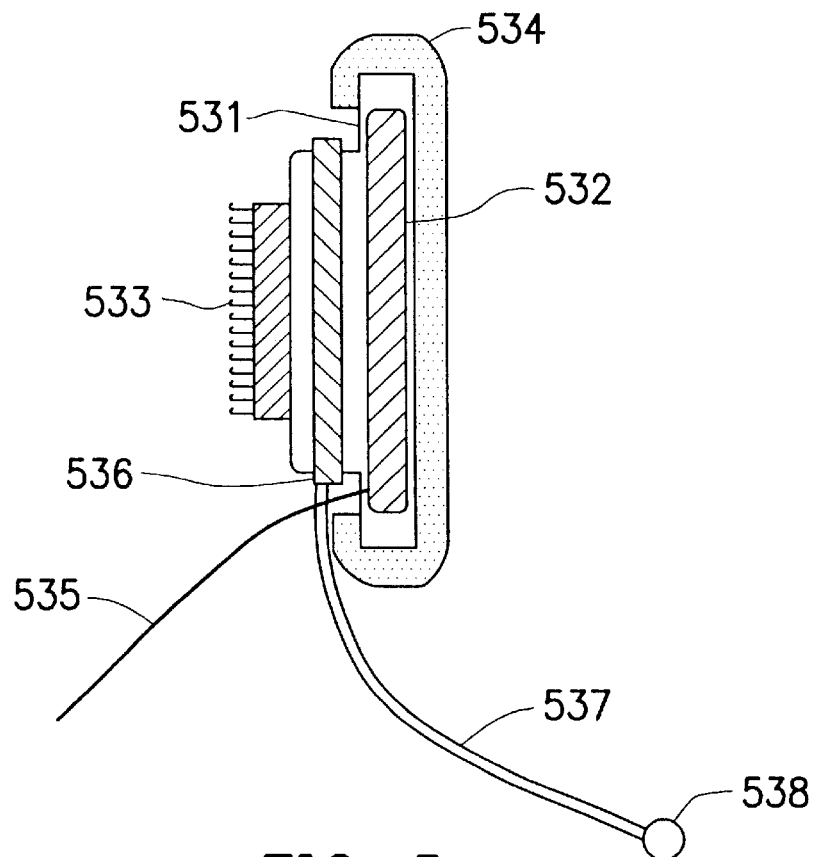
FIG. 5 is a sketch showing a microphone mounted next to an earphone according to this invention.

Due to the popularity of multimedia systems, using a microphone for conversational interaction while listening to a broadcast from an earphone is quite common. Therefore, it is often necessary to incorporate a microphone with an earphone. FIG. 5 is a sketch showing a microphone 538 mounted on an earphone 530 according to this invention.

As mentioned before, the earphone 530 has a speaker box 531, with a speaker 532 is installed inside. On the backside of the speaker box 531, there is a mounting structure 533 for engaging with the aforementioned mounting structure of the mounting cap 110 or the earmuff 120. The mounting structure 533 can be a Velcro magic tape. Furthermore, one side of the speaker box 531 for contact with the ear has a cushion 534 for increased comfort. The speaker 532 has a wiring cable 535, which connects with an external audio device. The microphone 538 has a slip ring 536 and a boom 537. The slip ring 536 can slide into the collar of the speaker box 531, and hence can rotate relative to the speaker box 531 as well.

With this design, the user is free to choose between hanging the earphone and the microphone on the left or right ear. Moreover, the microphone can be taken apart for easy storage. However, to prevent the microphone from turning over 360°, thereby over-twisting the wiring cable, both the slip-ring 536 and the speaker box 531 have stoppers (not shown in the figure) for limiting the angle of rotation. The boom 537 also has a certain degree of flexibility so that the user can bend the boom to the desired angle and curvature. A conductive wire leading from the microphone 538 can also run within the hollow interior of the boom 537. Finally, the conductive wire from the microphone 538 and the wiring cable 535 of the speaker 532 merge together before connecting with other external devices.

Figure 6:
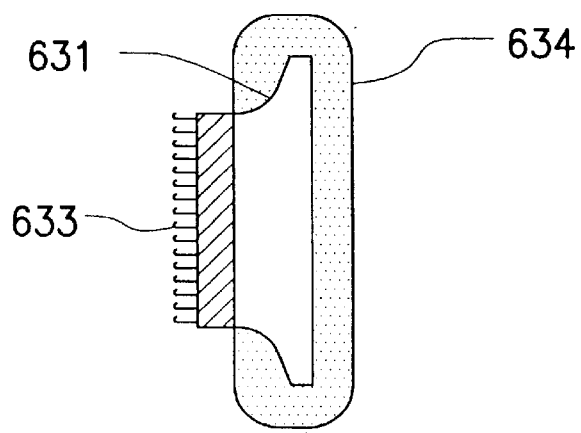
FIG. 6 is a sketch showing an ear cushion structure according to this invention.

Sometimes, when an earphone is used, stereo functions are not always necessary. Therefore, only one earphone on one side is required. If that is the case, an earphone can be mounted on any one terminal of the earphone clamping bar, and then an ear cushion can be mounted onto the other side for extra comfort. FIG. 6 is a sketch showing an ear cushion structure 630 according to this invention. The ear cushion 630 has an inner casing 631 for supporting an external cushioning pad 634. On the backside of the inner casing 631, there is a mounting structure 633 capable of engaging with the aforementioned mounting structures of the mounting cap 110 and the earmuff 120. Similarly, the mounting structure 633 can be a Velcro magic tape.

Figure 7:
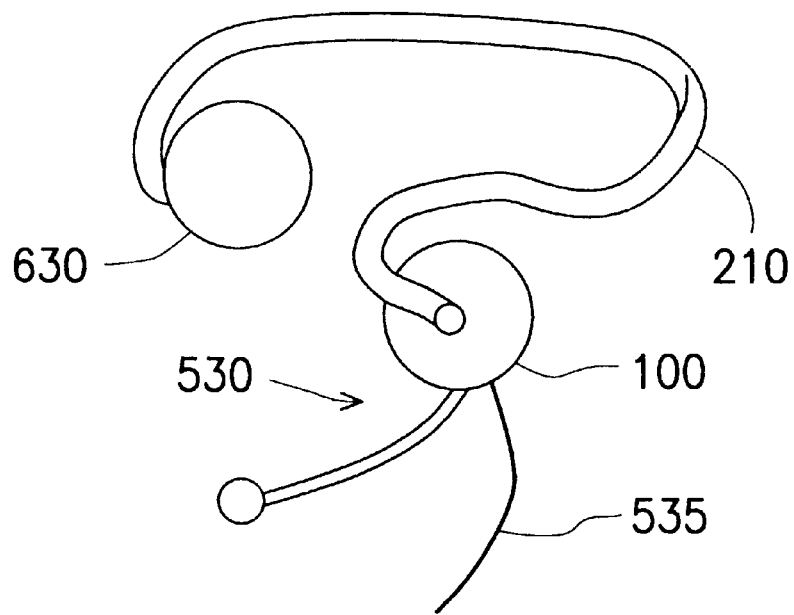
FIG. 7 is a sketch showing a complete assembly of the microphones, the earphones and the earmuffs mounted onto an earphone clamping bar according to this invention.

FIG. 7 is a sketch showing a complete assembly of an earphone with at microphone 530 and an ear cushion 630 mounted onto an earphone clamping bar 210 according to this invention. The earphone 530 must first be combined with the mounting cap 110 before the mounting cap 110 and the earphone clamping bar 210 are snapped together. Similarly, the ear cushion 630 must first be combined with the mounting cap 110 before the mounting cap 110 and the earphone clamping bar 210 are snapped together. Obviously, depending on the situation, an earmuff 120 can be added on as well.

Figure 8:
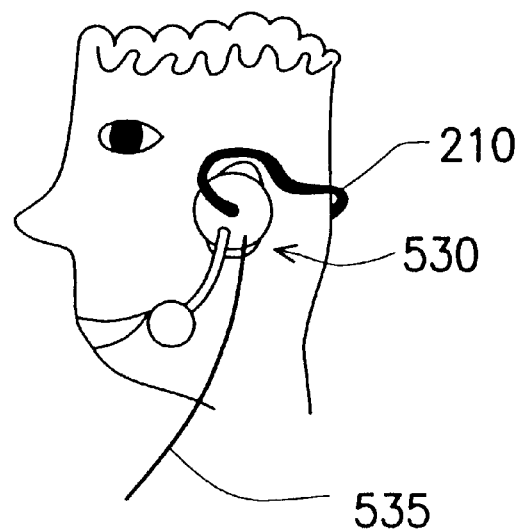
FIG. 8 is a sketch of the complete assembly as shown in FIG. 7 on a user's head.

As shown in FIG. 7, the earphone 530 is installed for hearing by the left ear and the ear cushion 630 is thereby installed on the right side. However, the user can reverse the arrangement by switching the earphone 530 and the ear cushion 630. After carrying out the switching between earphone and cushion, one can turn the microphone around towards the mouth of the user. Furthermore, a user can choose to use two earphones simultaneously with the microphone attached to one of the earphones. FIG. 8 is a sketch of the complete assembly as shown in FIG. 7 on a user's head.

The above embodiment of this invention illustrates that the earphone-microphone-earmuff assembly uses a mounting cap for joining earphone and earmuff together. Consequently, a user can choose between independently using earphones or earmuffs, or using them as a group. Alternatively, a user can choose to have a single earphone installed on one side for hearing, and then putting an ear cushion on the other side. Moreover, microphone can be mounted on the earphone whenever needed.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An earphone-microphone-earmuff assembly, comprising:

a mounting cap having an external mounting structure and an internal mounting structure, wherein the external mounting structure serves to connect with a pivot joint at one end of an earphone clamping bar, so that the mounting cap ultimately has three degrees of rotational freedom;

an earphone having an external mounting structure; and an earmuff whose exterior surface has an external mounting structure and whose interior surface has an internal mounting structure; and a plurality of different combinations of the mounting cap, the earphone and the earmuff in the following assemblages wherein:

the internal mounting structure of the mounting cap engages with the mounting structure of the earphone;

the internal mounting structure of the mounting cap engages with the external mounting structure of the earmuff; and the internal mounting structure of the mounting cap engages with the external mounting structure of the earmuff, and the internal mounting structure of the earmuff engages with the mounting structure of the earphone.

2. The assembly of claim 1, wherein the internal mounting structure of the mounting cap and the internal mounting structure of the earmuff includes female Velcro magic tape.

3. The assembly of claim 1, wherein the external mounting structure of the earmuff and the mounting structure of the earphone includes male Velcro magic tape.

4. The assembly of claim 1, wherein the external mounting structure of the mounting cap includes a ball joint and the end of the earphone clamping bar includes a ball socket so that the mounting cap can freely move to make the angle of the earphone-microphone-earmuff assembly fit the particular ear shape and facial curvature of a user.

5. The assembly of claim 1, wherein the earphone clamping bar extends backwards from the ear position around the back of the head so that the bar is positioned in the vicinity of the occipital ridge of the skull.

6. The assembly of claim 1, wherein the earphone further includes a speaker and a speaker box, the speaker is enclosed inside the speaker box, the speaker is connected to an audio device through a wiring cable, and the mounting structure of the earphone is furthermore fixed onto an exterior surface of the speaker box.

7. The assembly of claim 6, wherein the wiring cable is electrically connected to the audio device through a plug.

8. The assembly of claim 6, wherein a soft cushion is mounted over the exterior surface of the speaker box where ear contact is made so that the user can enjoy extra comfort.

9. The assembly of claim 6, wherein the exterior of the speaker box further includes a mounting structure for engaging with the mounting structure of a microphone, so that after the two mounting structures are engaged, the microphone can rotate within a certain pre-defined angular range relative to the speaker box.

10. The assembly of claim 1, where the assembly further includes an ear cushion assembly that can be used as a substitute for an earphone, and the ear cushion has an inner casing for support and a cushioning pad outside.

11. The assembly of claim 1, wherein the earmuff includes an inner flap and earmuff warmer such that the earmuff warmer wraps around the inner flap.

12. An earphone-microphone-earmuff assembly, comprising:
   a mounting cap having an external mounting structure and an internal mounting structure, wherein the external mounting structure is used for uniting with a pivot joint at one end of an earphone clamping bar, so that the mounting cap ultimately has three degrees of rotational freedom;
   an earphone that includes a speaker, a speaker box and a mounting structure, wherein the speaker is installed inside the speaker box and the mounting structure is fixed onto a surface on the outside of the speaker box; and
   an earmuff that includes an inner flap and an earmuff warmer, wherein the earmuff warmer encloses the inner flap, the exterior surface of the inner flap has an external mounting structure, and the interior surface of the inner flap has an internal mounting structure; and
   a plurality of different combinations of the mounting cap, the earphone and the earmuff in the following assemblages wherein:
      the internal mounting structure of the mounting cap engages with the mounting structure of the earphone;
      the internal mounting structure of the mounting cap engages with the external mounting structure of the earmuff; and
      the internal mounting structure of the mounting cap engages with the external mounting structure of the earmuff, and the internal mounting structure of the earmuff engages with the mounting structure of the earphone.

13. The assembly of claim 12, wherein the internal mounting structure of the mounting cap and the internal mounting structure of the earmuff includes female Velcro magic tape.

14. The assembly of claim 12, wherein the external mounting structure of the earmuff and the mounting structure of the earphone includes male Velcro magic tape.

15. The assembly of claim 12, wherein the external mounting structure of the mounting cap includes a ball joint and the end of the earphone clamping bar includes a ball socket so that the mounting cap can freely move to make the angle of the earphone-microphone-earmuff assembly fit the particular ear shape and facial curvature of a user.

16. The assembly of claim 12, wherein the earphone clamping bar extends backwards from the ear position around the back of the head so that the bar is positioned in the vicinity of the occipital ridge of the skull.

17. The assembly of claim 12, wherein the earphone is connected to the audio device through a piece of wiring cable and a plug.

18. The assembly of claim 12, wherein the exterior of the speaker box further includes a mounting structure for engaging with the mounting structure of a microphone, so that after the two mounting structures are engaged, the microphone can rotate within a certain pre-defined angular range relative to the speaker box.

19. The assembly of claim 12, wherein the assembly further includes an ear cushion assembly that can be used as a substitute for an earphone, the ear cushion has an inner casing for support, a cushioning pad outside and a mounting structure on the exterior surface of the inner casing for engaging with the mounting cap.

20. The assembly of claim 12, wherein a soft cushion is mounted over the exterior surface of the speaker box where ear contact is made so that the user can enjoy extra comfort.

* * * * *